United States Patent [19]

Milliken et al.

[11] 4,180,066

[45] Dec. 25, 1979

[54] SAFETY INTERFACE AND VALVE FOR ANESTHESIA GAS SCAVENGING

[75] Inventors: Ralph A. Milliken, Spring Valley, N.Y.; Terence D. Wall, Hackensack, N.J.; Martin Boelens, Zaandam, Netherlands

[73] Assignee: Vital Signs, Inc., East Rutherford, N.J.

[21] Appl. No.: 844,045

[22] Filed: Oct. 20, 1977

[51] Int. Cl.² ............................................. A61M 16/00
[52] U.S. Cl. ......................... 128/205.24; 128/205.17; 137/493.1; 137/526; 137/568; 128/204.18
[58] Field of Search .................. 128/188, 145.8, 145.6, 128/145.7, 145.5; 137/493.1, 493.2, 526, 568

[56] References Cited

U.S. PATENT DOCUMENTS

| | | | |
|---|---|---|---|
| 2,809,659 | 10/1957 | Gillespie et al. | 137/526 X |
| 3,088,456 | 5/1963 | Stanton | 128/202 X |
| 3,721,239 | 3/1973 | Myers | 128/188 |
| 3,800,793 | 4/1974 | Marrese et al. | 128/188 |
| 3,993,059 | 11/1976 | Sjöstrand | 128/145.8 |

FOREIGN PATENT DOCUMENTS 312352  12/1955  Switzerland ........................ 137/493.1

*Primary Examiner*—Henry J. Recla
*Attorney, Agent, or Firm*—Norbert P. Holler

[57] ABSTRACT

A safety interface for connection between an anesthesia patient circuit and a disposal system, and a combined positive and negative pressure relief valve for the safety interface.

The safety interface comprises a housing defining a passageway, means for connecting an upstream end of the passageway to the waste anesthetic gas outlet of an anesthesia patient circuit, means for connecting the downstream end of the passageway to a disposal system, a negative pressure relief valve and a positive pressure relief valve in communication with the passageway. The positive pressure release valve and negative pressure release valve are preferably provided in the form of a combined positive and negative pressure release valve, and a second negative pressure release valve is preferably also provided. Preferably, a restrictor partially obstructs the passageway at a point on its upstream to downstream extent, and the positive pressure relief valve communicates with the passageway at a point downstream of the restrictor. Means for connecting a reservoir in communication with the passageway upstream of the restrictor are preferably provided.

The double acting pressure relief valve comprises a spindle, a first disc mounted on the spindle, a spindle receptacle for supporting said spindle, a coil spring seated in said spindle receptacle and surrounding said spindle, and a second disc having at least one aperture therein which may be closed by contact with said first disc, said second disc slidingly engaging said spindle and situated between said first disc and said spindle receptacle. The coil spring biases the second disc towards the housing so that the second disc may engage a raised ridge surrounding an opening in the housing.

8 Claims, 6 Drawing Figures

SAFETY INTERFACE AND VALVE FOR ANESTHESIA GAS SCAVENGING

BACKGROUND OF THE INVENTION

The instant invention relates to an anesthesia system and more particularly to a safety interface and valve for anesthesia gas scavenging.

Since 1929 evidence has been accumulating in the international medical literature indicating that the chronic exposure to waste anesthetic gases in subanesthetizing concentrations is harmful to operating room personnel. The evidence indicates that female operating room personnel are subject to a significantly higher incidence of spontaneous abortions, involuntary infertility, congenital defects in children born subsequent to operating room employment and malignant tumors of the lymphoid and reticuloendothelial system, and both sexes are subject to a higher incidence of liver disease. The international and American research is well summarized in the National Institute for Occupational Safety and Health (NIOSH) document entitled "Criteria for a Recommended Standard Occupational Exposure to Waste Anesthetic Gases and Vapors,"HEW (NIOSH) Publication #77-140, March, 1977. Additional research work continues at this time. Recognizing this hazard, the federal Food and Drug Administration has required that all proposed volatile anesthetic agents before introduction into the market place be tested for possible carcinogenicity and mutagenicity. The National Institute for Occupational Safety and Health continues to fund additional studies relating to operating room hazards and their control. The Department of Labor's Occupational Safety and Health Administration (OSHA) is now reviewing the NIOSH Criteria Document and will consider requiring safety devices to be placed in operating rooms to protect all personnel potentially exposed. The Joint Commission on the Accreditation of Hospitals already mandates waste anesthesia gas scavening as a criterion for approval of a hospital Anesthesia Service.

Accordingly, the instant invention is designed to interface between the disposal point and the gas scavenging devices attached to the anesthesia patient circuit or anesthesia ventilator. By providing built-in positive and negative pressure relief valves, the instant invention helps protect both patient and operating room personnel from hazards of defective or inoperative gas scavenging systems and inadequate gas scavenging.

BRIEF SUMMARY OF THE INVENTION

The instant invention provides, when used in an anesthesia gas scavenging system, a safety interface between an anesthesia patient circuit and a disposal system, and a double acting pressure relief valve for the safety interface. The safety interface comprises a housing defining a passageway having an upstream end and a downstream end, means for connecting the upstream end of the passageway to the waste anesthetic gas outlet of an anesthesia patient circuit, means for connecting the downstream end of the passageway to a disposal system, a first negative pressure relief valve in communication with the passageway, and a positive pressure relief valve in communication with the passageway. Preferably, a restrictor partially obstructs the passageway at a point on its upstream to downstream extent, and the positive pressure relief valve communicates with the passageway at a point downstream of the restrictor. Preferably, the first negative pressure relief valve and the positive pressure release valve are provided in the form of a combined positive and negative pressure release valve, and a second negative pressure release valve is also provided. Preferably, the second negative pressure relief valve communicates with the passageway at a point upstream of the restrictor. Preferably, a chimney is provided and extends outwardly from the housing so that the bore of the chimney is in communication with the passageway, with the combined positive and negative pressure release valve arranged to interrupt the communication between the bore of the chimney and the passageway.

The double acting pressure relief valve comprises a spindle, a first disc mounted on the spindle, a spindle receptacle for supporting said spindle, said spindle receptacle having a pocket having an open end, means for securing the receptacle to the housing of the safety interface so that the open end of the pocket confronts an opening in the housing, coil spring seated in said spindle receptacle and surrounding at least an end portion of said spindle in slidable relation therewith, and a second disc having at least one aperture therein which may be closed by contact with said first disc, said second disc slidingly engaging said spindle and situated between said first disc and said spindle receptacle. The coil spring biases the second disc towards the housing so that second disc may engage a raised ridge on the housing surrounding the opening.

BRIEF DESCRIPTION OF THE DRAWINGS

FIG. 5 is an exploded view of the valve shown in FIG. 3; and

FIG. 6 is an enlarged sectional view taken on the horizontal plane indicated by the line 6—6 in FIG. 2.

DESCRIPTION OF THE PREFERRED EMBODIMENT

Figure 1:
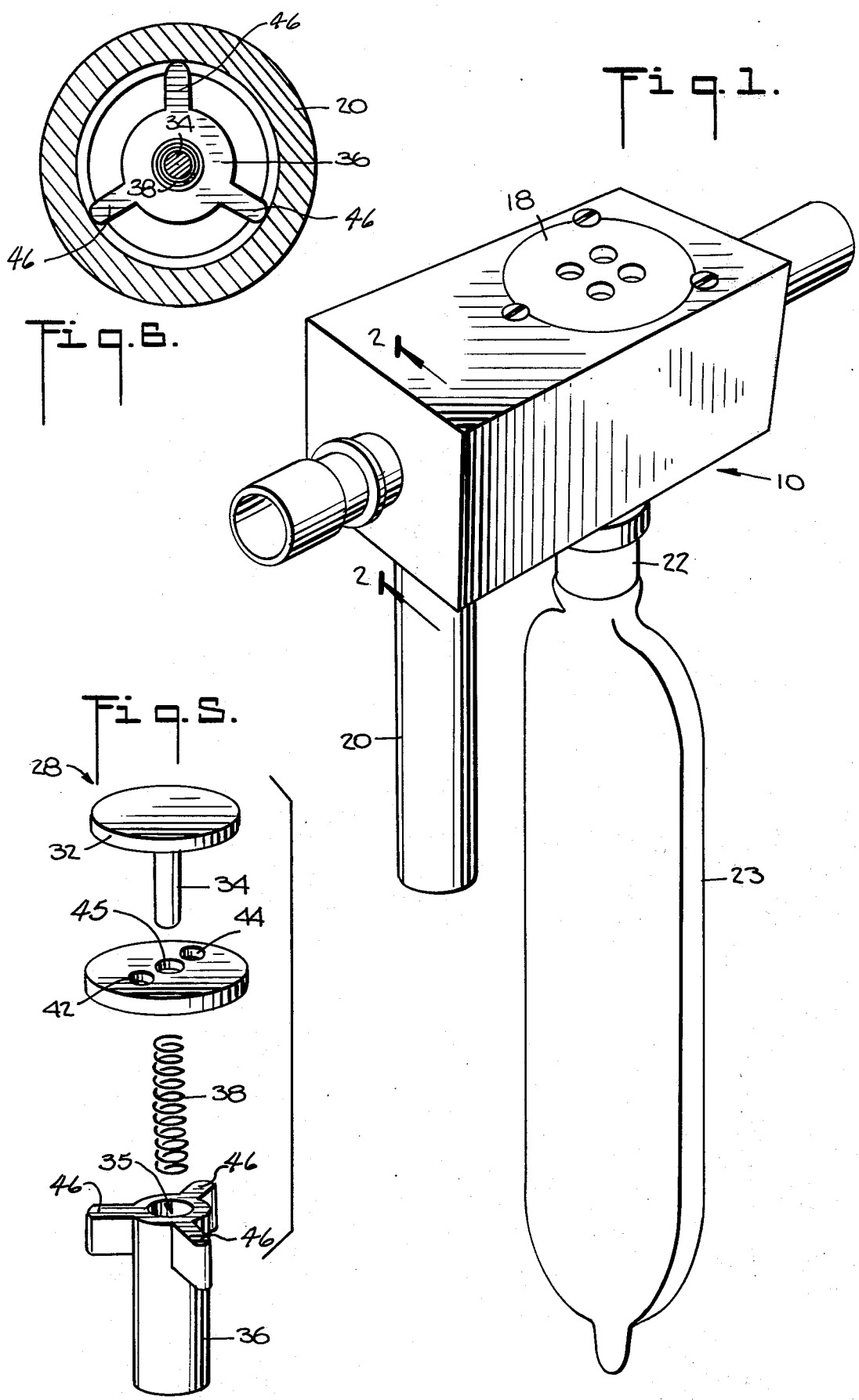
FIG. 1 is a perspective view of a safety interface in accordance with the instant invention.
Figure 2:
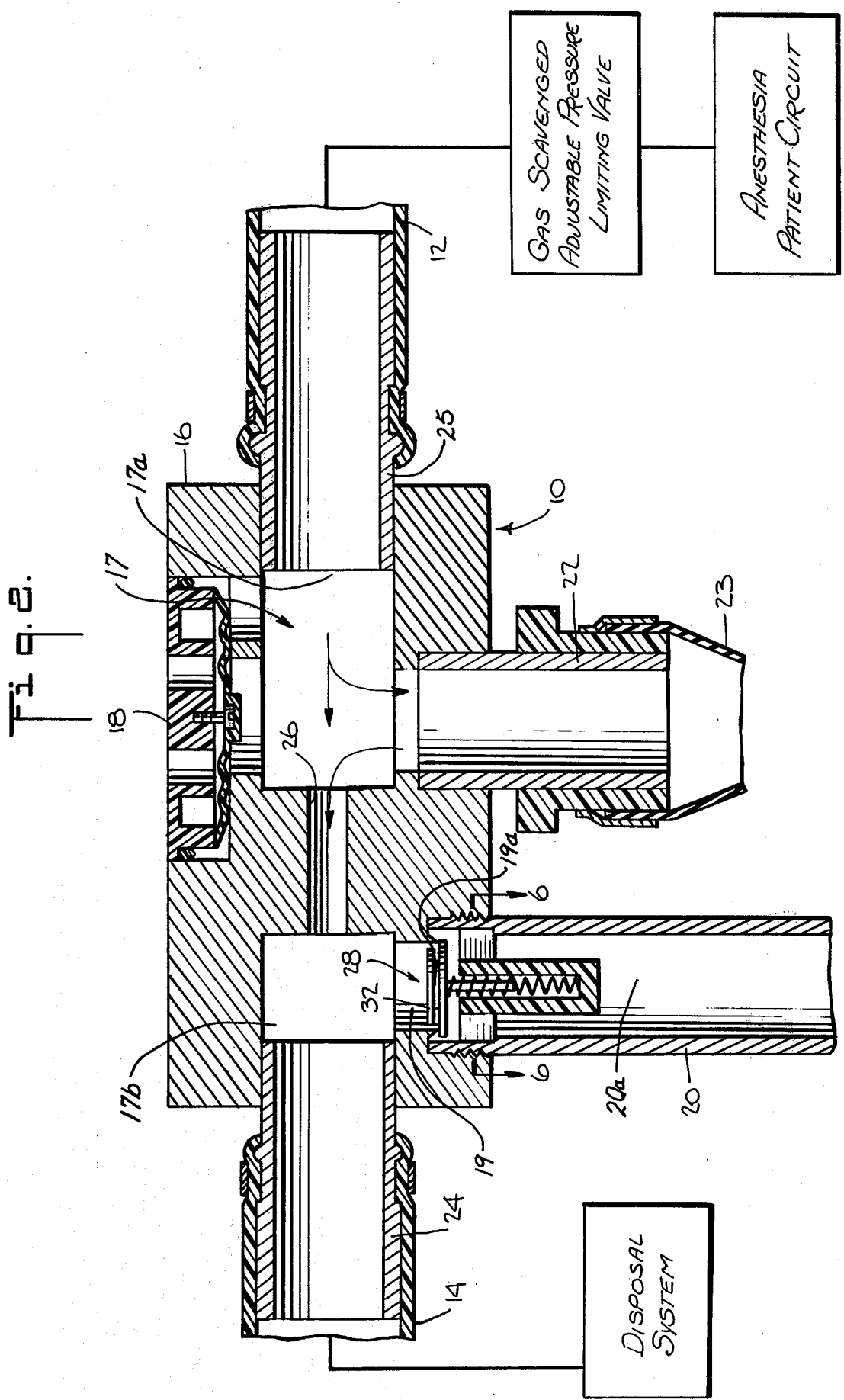
FIG. 2 is a central, vertical sectional, enlarged view of the safety interface shown in FIG. 1 taken along line 2—2 in FIG. 1.

In describing the preferred embodiment of the instant invention, reference is made to the drawings, wherein the inventive safety interface 10 is shown in FIGS. 1 and 2. As shown in FIG. 2, when in use, the interface 10 is connected at one end to a transfer tubing 12 which in turn is connected to a gas scavenged adjustable pressure limiting valve which in turn is connected to an anesthesia patient circuit and which thus serves as the waste anesthetic gas outlet of the anesthesia patient circuit.

At the other end the interface 10 connects with disposal tubing 14 which in turn connects with a disposal system. The interface 10 includes a non-rusting metal housing 16 which defines a passageway 17 having an upstream end 17a and a downstream end 17b. A conventional, adjustable, negative pressure relief valve 18 is mounted in the housing and communicates with the passageway 17. A tubular reservoir bag mount 22 is affixed to the housing and is in communication with the passageway 17. Thus, the bag mount 22 provides means for connecting a reservoir bag 23 to the passageway 17 in communication therewith. A tubular removable outlet 24 is affixed to the housing 16 and is in communication with the downstream end 17b of the passageway 17. A tubular inlet 25 is in communication with the upstream end 17a of passageway 17. As shown in FIG. 2, the inlet 25 serves as a means for connecting the upstream end of the passageway 17 to the waste anesthetic gas outlet of the anesthesia patient circuit, and the outlet 24 serves as a means for connecting the downstream end of the passageway 17 to a disposal system.

Figure 3:
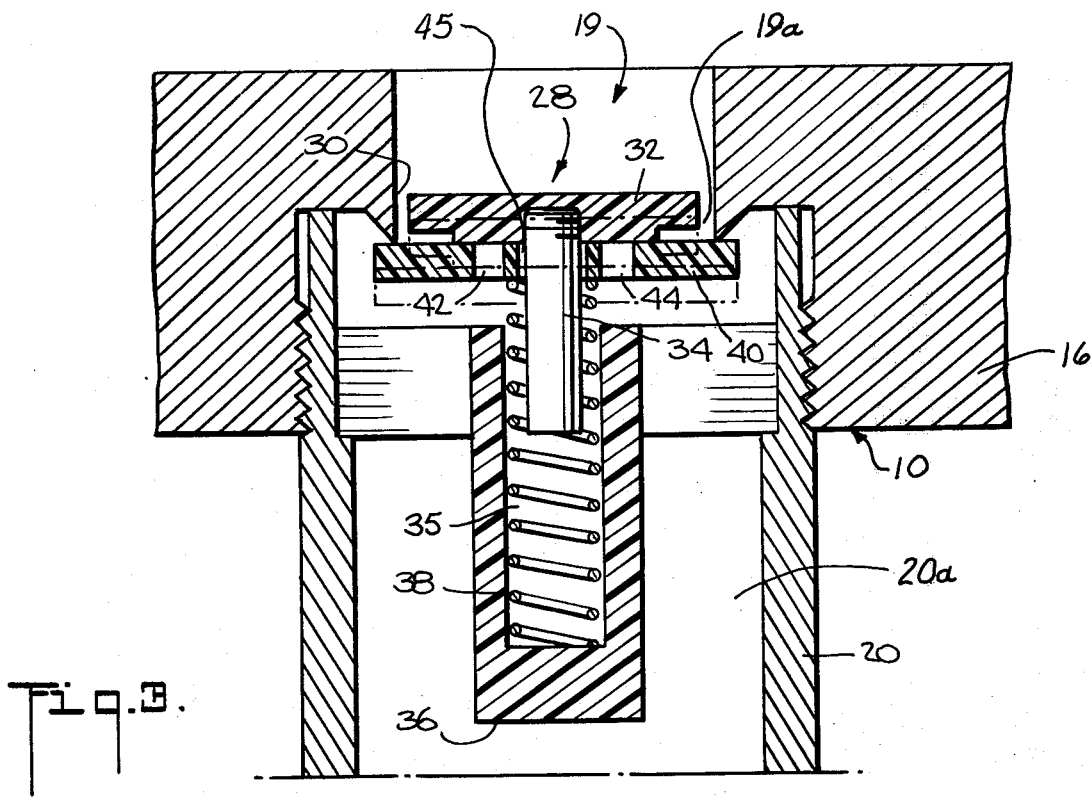
FIG. 3 is an enlarged, central, vertical sectional view of the double action pressure relief valve situated at the top of the chimney within the patient safety interface shown in FIG. 1, the valve being shown in its closed position.
Figure 4:
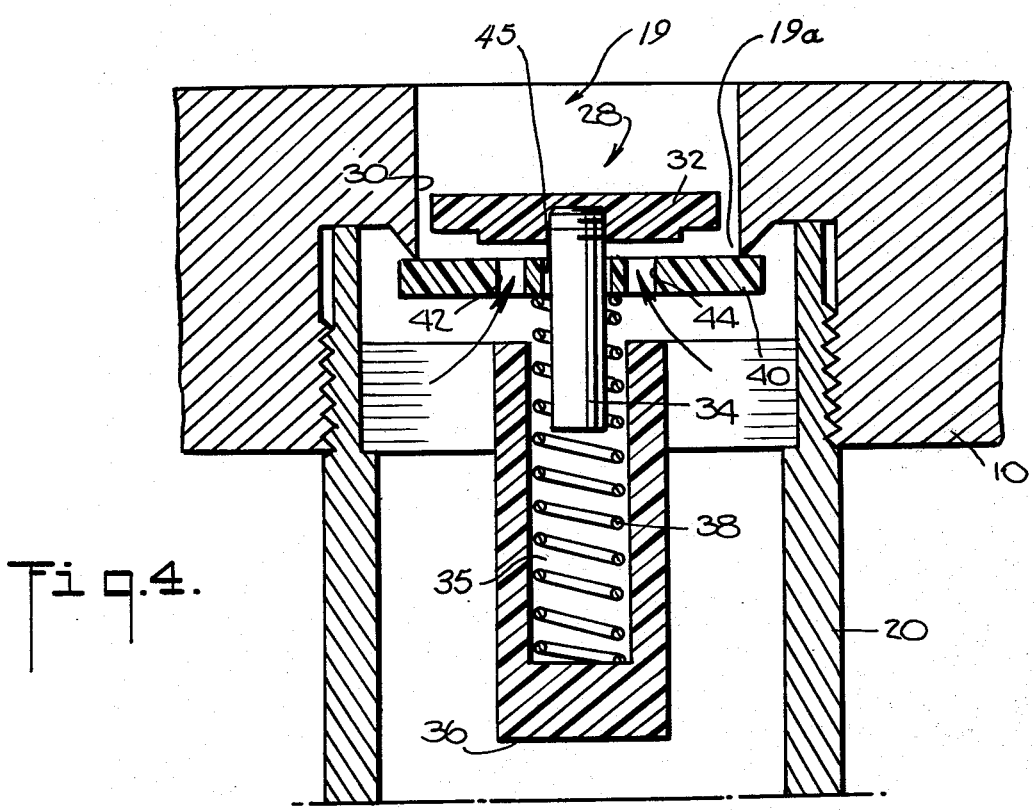
FIG. 4 is the same as FIG. 3, but shows the valve opened in response to a partial vacuum created within the interface.

A port 19 formed in housing 16 extends from the passageway 17 to an opening 19a. A tubular chimney 20 is affixed to the housing 16 so that the bore 20a of the chimney is in communication with the opening 19a. A restrictor 26, formed intergrally with housing 16, partially obstructs the passageway 17 at a point along its upstream to downstream extent. The combined positive and negative pressure relief valve 28 is arranged to interrupt the communication between the opening 19a and the bore 20a of the chimney. As best seen in FIGS. 3 and 4, the valve 28 incorporates a raised seating ridge 30, which is formed integrally with the housing and which surrounds the opening 19a of port 19 and also includes a first disc 32 mounted on a spindle 34 which extends into a pocket 35 formed in spindle receptacle 36. The spindle 34 is accompanied by a spring 38 which also sits in the pocket 35 of spindle receptacle 36. A second disc 40 having two apertures 42 and 44 underlies the first disc 32. As best seen in FIG. 6, the spindle receptacle 36 is fixedly secured within the chimney 20 by three equi-distant arms 46.

As shown in FIGS. 3 and 4 the spring 38 surrounds the end portion of spindle 34 remote from the first disc 32. The spring 38 is in slidable relation with the spindle 34. The interior diameter of the coil spring 38 is greater than the diameter of the spindle 34, so that there is some clearance between the spindle and the inside of the spring. The coil spring 38 is engaged with the second disc 40, and biases the second disc 40 towards the housing 16, so that the second disc 40 may bear against the raised ridge 30 surrounding the opening 19a of the housing. As also shown in FIGS. 3 and 4, the spindle 34 extends through a hole 45 in the second disc 40. The interior diameter of this hole 45 is greater than the diameter of the spindle, so that the spindle 34 may slide relative to the second disc 40.

In using the instant invention, the interface 10 is connected to a gas scavenged adjustable pressure limiting valve of an anesthesia patient circuit by means of the transfer tubing 12 and to a disposal system by means of the removable outlet 24 and disposal tubing 14 (see FIG. 2). Under optimum conditions, the combined positive and negative pressure relief valve 28 is closed as seen in FIG. 3. The first disc 32 overlies all of the apertures in the second disc 40, the second disc 40 lies in abutting engagement with the raised ridge 30, and the waste anesthetic gases flow through the interface 10 to the disposal system in the direction indicated by the arrow in FIG. 2. The disposal system may be either active or passive, an active disposal system being one in which exerts negative pressure on the interface, and a passive disposal system is one in which the waste gases flow to the end of the disposal tubing 14 by the positive pressure generated in the anesthesia patient circuit.

When the disposal system or disposal tubing 14 become non-functional owing to occlusion of the tubing or discontinuity in the disposal system, the waste anesthetic gas will be stored in the reservoir bag 23 which then assumes a distended shape, which signifies system malfunction. If additional gas enters the interface 10, and the pressure in the passageway increases to a sufficient extent to overcome the resistance of the spring 38, the gas will be permitted to enter the room through the pressure relief valve 28 and chimney 20. This gas will enter the room by moving the first disc 32 and the second disc 40 downward from the position shown in FIG. 3, allowing gas to escape between the disc 40 and the seating ridge 30. This action of the combined valve 28 as a positive pressure relief valve will limit any buildup of positive pressure within the passageway 17 to no more than a predetermined amount, and therefore will prevent the imposition of any excessive back pressure on the anesthesia patient circuit.

When using an active disposal system, it is a possibility that life-sustaining gases will be drawn out of the anesthesia patient circuit, thereby risking the patient's life. To prevent this occurrence, two negative pressure relief valves are provided. The combined positive and negative pressure relief valve 28 serves as a first negative pressure relief valve, and the valve 18 is a second negative pressure release valve. In the action of valve 28 as a negative pressure release valve, as best seen in FIG. 4, the first disc 32 lifts up from its normal closed, abutting relationship with the second disc 40 (shown in FIG. 3), exposing the two apertures 42, 44 and allows room air to enter the disposal system, thereby preventing excessive negative pressure. If the vacuum exerted creates a flow in excess of the capacity of the pressure relief valve 28, then the conventional negative pressure relief valve 18 will open to provide additional room air to satisfy the flow/pressure requirements of the active disposal system.

In the event of extraordinarily large flows of gas from the anesthesia patient circuit, the reservoir bag 23 can contain these gases until the disposal system can accept them.

What is claimed is:

1. A safety interface for connection between an anesthesia patient circuit and a disposal system, said interface comprising:
  (a) a housing defining a passageway having an upstream end and a downstream end, said passageway having a restrictor between said upstream and downstream ends partially obstructing flow therethrough, said housing also defining a port extending from the downstream end of the passageway to an opening on the exterior of said housing, said housing including a raised ridge surrounding said opening;
  (b) means for connecting the upstream end of said passageway to the waste anesthetic gas outlet of an anesthesia patient circuit;
  (c) means for connecting the downstream end of said passageway to a disposal system;
  (d) means for connecting a reservoir to the upstream end of said passageway;
  (e) negative pressure relief valve means in communication with said passageway and responsive to a negative pressure therein;
  (f) a chimney affixed to said housing and extending outwardly therefrom, so that the bore of said chimney is in communication with said opening;

(g) combined positive and negative pressure relief valve means responsive to positive and negative pressures in said passageway and constructed and arranged to interrupt the communication between said opening and the bore of said chimney said combined valve means including:

a spindle;

a first disc mounted on said spindle;

a spindle receptacle secured to the inside of said chimney and defining a pocket having an open end confronting said opening;

a coil spring seated in the pocket of said spindle receptacle and surrounding at least an end portion of said spindle in slidable relation therewith; and a second disc having at least one aperture therein, said second disc slidably engaging said spindle and situated between said first disc and said spindle receptacle, said spring engaging said second disc and biasing said second disk towards said housing, said second disk being constructed and arranged for abutting engagement with said raised ridge, said first disk being constructed and arranged to be located within said opening and overly all of the apertures in said second disk, and (h) said negative pressure relief valve means opening in response to a greater negative pressure than said negative pressure to which the negative pressure relief valve portion of said combined positive and negative pressure relief valve means is responsive.

2. The safety interface of claim 1 wherein said spindle receptacle includes a body defining said pocket and three equi-distant arms extending from said body to the interior surface of said chimney.

3. A safety interface as claimed in claim 1, wherein said negative pressure relief valve means communicates with the upstream end of said passageway.

4. A safety interface for connection between an anesthesia patient circuit and a disposal system, said interface comprising:

(a) a housing defining a passageway, said passageway having an upstream end and a downstream end;

(b) means for connecting the upstream end of said passageway to the waste anesthetic gas outlet of an anesthesia patient circuit;

(c) means for connecting the downstream end of said passageway to a disposal system;

(d) a first negative pressure relief valve in communication with said passageway;

(e) a restrictor partially obstructing said passageway at a point on its upstream-to-downstream extent;

(f) a positive pressure relief valve in communication with said passageway at a point downstream of said restrictor, and (g) means for connecting a reservoir in communication with said passageway at a point upstream of said restrictor.

5. An interface as claimed in claim 4 further comprising an enclosed reservoir in communication with said passageway at a point upstream of said restrictor and connected to said passageway by way of said means for connecting a reservoir.

6. An interface as claimed in claim 5 wherein said reservoir is a distensible bag.

7. An interface as claimed in claim 4, further comprising a second negative pressure relief valve in communication with said passageway.

8. An interface as claimed in claim 7 wherein said first negative pressure relief valve and said positive pressure relief valve constitute a combined positive and negative pressure relief valve.

* * * * *